United States Patent [19]
Howell

[11] Patent Number: 5,817,914
[45] Date of Patent: Oct. 6, 1998

[54] INBRED CORN LINE NP 993

[75] Inventor: Monroe E. Howell, Savannah, Mich.

[73] Assignee: Novartis Finance Corporation, New York, N.Y.

[21] Appl. No.: 732,008

[22] Filed: Oct. 16, 1996

Related U.S. Application Data

[63] Continuation of Ser. No. 573,164, Dec. 15, 1995.

[51] Int. Cl.[6] .............................. A01H 4/00; A01H 5/00; A01H 1/00; C12N 5/04
[52] U.S. Cl. .................. 800/200; 800/250; 800/DIG. 56; 47/58; 47/DIG. 1; 435/412; 435/424; 435/430; 435/430.1
[58] Field of Search ...................................... 800/200, 205, 800/250, DIG. 56; 47/58, DIG. 1; 435/172.3, 172.1, 424, 430

*Primary Examiner*—Gary Benzion
*Attorney, Agent, or Firm*—Thomas Hoxie, Esq.

[57] ABSTRACT

An inbred corn line, designated NP 993, is disclosed. The invention relates to the seeds of inbred corn line NP 993, to the plants of inbred corn line NP 993 and to methods for producing a corn plant produced by crossing inbred line NP 993 with itself or with another corn plant. The invention further relates to hybrid corn seeds and plants produced by crossing inbred line NP 993 with another corn line.

16 Claims, No Drawings

INBRED CORN LINE NP 993

This is a CONTINUATION of application Ser. No. 08/573,164, filed on Dec. 15, 1995.

BACKGROUND OF THE INVENTION

This invention relates to a new and distinctive corn inbred line designated NP 993 and to hybrids made by using NP 993 as a parent.

Corn (*Zea mays*) is a valuable and important field crop. Thus, plant breeders are continually developing new and superior corn inbred lines for production of high yielding, agronomically sound hybrids. The goal of the plant breeder is to combine in a single variety or hybrid an improved combination of desirable traits from the parent germplasm. These traits may include maximization of yield, resistance to disease and insects, tolerance to drought, heat and other environmental stresses.

Corn hybrid development requires the development of homozygous inbred lines, the crossing of these lines, and the subsequent evaluation of those crosses. Pedigree, backcross, and recurrent selection breeding methods are used to develop inbred lines from breeding populations. Breeding programs combine the genetic backgrounds from two or more inbred lines or various other genetic sources into breeding pools from which new inbred lines are developed by self pollination and selection of desired phenotypes. The new inbred lines are crossed with other inbred lines, and hybrids from these crosses are evaluated to determine which have commercial potential.

Once the inbred parents that give a superior hybrid are identified, the hybrid seed can be reproduced indefinitely as long as inbred parent homogeneity is maintained. Corn hybrids may be either single cross hybrids, produced when two inbred lines are crossed to produce the first generation ($F_1$) progeny; double cross hybrids, produced from four inbred lines crossed in pairs (A×B and C×D) and then the two $F_1$ hybrids are crossed again (A×B)×(C×D); or three-way cross hybrids produced from crossing a single cross (A×B) to a third inbred line C. Numerous references are available on the topic of corn breeding and hybrid seed corn production. Those skilled in the art of corn breeding and production are well aware of techniques and methods for the development of inbred corn lines and corn hybrids. Reference is made particularly to Corn and Corn Improvement, Third Edition, ed. G. F. Sprague and J. W. Dudley, American Society of Agronomy Monograph No. 18, particularly chapters 8 and 9, the substantive content of which is hereby incorporated by reference.

SUMMARY OF THE INVENTION

According to the invention, there is provided a novel inbred corn line, designated NP 993. This invention thus relates to the seeds of inbred corn line NP 993, to the plants of inbred corn line NP 993 and to methods of producing a corn plant comprising the crossing of inbred line NP 993 with itself or another corn line. This invention further relates to hybrid corn seed and plants produced by crossing the inbred line NP 993 with another corn inbred line.

DEFINITIONS

In the description and examples that follow a number of terms are used; therefore, to provide a clear and consistent understanding of the specification and claims the following definitions are provided.

RK=Round Kernels: the percentage of kernels that do not pass through a 13/64 slotted screen.

HE=Husk Extension: the length (cm) of the husk past the ear tip at maturity.

NN=Node Number: the number of nodes of the entire plant.

PRM=Predicted Relative Maturity. This trait is based on the harvest moisture of the grain. The relative maturity rating is based on a known set of checks, and is referred to as the Minnesota Relative Rating System.

MST=Harvest Moisture. The moisture is the actual percentage moisture of the grain at harvest.

STK (BR)=The percentage of plants broken below the ear at harvest.

YLD=Yield; bushels per acre. The actual yield of the grain at harvest (bu/a) adjusted to approximately 15.5% moisture.

RT=Number of plants lodged (leaning from vertical but not broken).

Plt. Ht.=Plant Height; The length of the plant to tassel tip (cm).

$$HU = \text{Heat Units}; \frac{\text{Max Temp } (\leq 86° \text{ F.}) + \text{Min Temp } (\geq 50° \text{ F.})}{2} - 50$$

Ear Ht.=Ear Height. The measurement from the ground to the top developed ear node attachment measured in cm.

DETAILED DESCRIPTION OF THE INVENTION

Inbred corn line NP 993 is a yellow dent inbred line with superior characteristics and is best suited as a male in crosses for production of first generation ($F_1$) corn hybrids. NP 993 is best adapted to the North Central part of the United States. NP 993 can be used to produce hybrids from approximately 95 to 115 days relative maturity based on the Minnesota Relative Maturity Rating System for harvest of grain. Inbred line NP 993 has demonstrated good combining ability with families derived from Iowa Stiff Stalk, for example, B14 and related lines.

Inbred corn line NP 993 was derived from selfing Pioneer Hybrid 3737 (P3737) commercially available from Pioneer Hi-Bred International, Inc. Self-pollination and selection were practiced within the above $F_1$ hybrid P3737 for seven generations in the development of NP 993. During the development of the line, crosses of segregating families were made to inbred testers to evaluate combining ability. Inbred line NP 993 can be reproduced by planting seeds of the line, growing the resulting corn plants under self-pollination or sib-pollination conditions with adequate isolation and then harvesting the resulting seed. No variant traits have been observed or are expected in NP 993.

The inbred line has been evaluated at numerous research stations across the Northern United States Corn Belt and Canada. Inbred line NP 993 has shown uniformity and stability for all discernible characteristics as described in the following variety description. The description is based on data collected primarily at Stanton, Minn., Washington, Iowa and Janesville, Wis. on a maximum of 9 replications. In interpreting the color designations herein, reference is made to the Munsell Glossy Book of Color, a standard color reference.

TABLE 1

VARIETY DESCRIPTION INFORMATION FOR INBRED LINE NP 993, NP 899 and A619

|  | NP 993 | NP 899 |  |
| --- | --- | --- | --- |
| Type: | Dent | Dent | A619 |
| Region Best Adapted: | Northcentral | Northern and Central | Dent |

A. Maturity:

|  |  |  |  |
| --- | --- | --- | --- |
| HU to Silk (HUS): | 1474 | 1513 | — |
| HU to pollen: | 1390 | 1463 | — |

B. Plant Characteristics:

|  |  |  |  |
| --- | --- | --- | --- |
| Plant height (to tassel tip) (cm): | 160.1 | 221 | 201.6 |
| Length to top ear internode (cm): | 11.2 | 15 | 14.3 |
| Ear height (to base of top ear internode) (cm): | 43.8 | 81 | 52.1 |
| Number of tillers: | 0 | 0 | 0 |
| Number of ears per stalk: | 1.2 | 1.0 | 1.0 |
| Cytoplasm type: | Normal | Normal |  |

C. Leaf:

|  |  |  |  |
| --- | --- | --- | --- |
| Color: | Medium green (7.5GY/4/4) | Light green (HY) | Medium Green (7.5GY/4/4) |
| Angle from stalk (upper half): | 27° | 30–60° | 22° |
| Number of leaves- above top ear (mature plants): | 5 | — | 5 |
| Marginal waves: | Few (3) | Few | Medium (4) |
| Width (widest point of ear node leaf) (cm): | 10.8 | 10 | 9.0 |
| Sheath Pubescence: | Slight-medium (3) | Light |  |
| Longitudinal creases: | Few (3) | Few | Few (3) |
| Length (ear node leaf) (cm): | 67.3 | 75 | 67.2 |

D. Tassel:

|  |  |  |  |
| --- | --- | --- | --- |
| Number of lateral branches: | 9 | 9 | 9.4 |
| Branch angle from central spike: | 50° | 30–40° | 30–35° |
| Pollen shed: | (7) Medium-heavy | Heavy | (7) Medium-Heavy |
| Anther color: | Green-yellow (2.5GY/8/6) | Purple | Green-Yellow |
| Glume color: | Variegated (5 GY/5/6, 5R/3/6) | Medium Green | Medium Green |
| Tassel length: | 40.8 cm | — | 44.1 cm |

E. Ear (Husked ear data except where stated otherwise):

|  |  |  |  |
| --- | --- | --- | --- |
| Length (cm): | 14.8 | 16 | 14.0 |
| Weight (gm): | 95.7 | 80 | 101.8 |
| Midpoint diameter (mm): | 38.2 | 37 | 48.2 |
| Kernel rows: | 15.3 Distinct, Straight | 16 Distinct, Straight | 15.6 Indistinct Straight |
| Silk color: | Green-yellow (2.5GY/8/6) | Pink | Green-Yellow (25GY/8/6) |
| Husk extension: | Short-ears exposed | Long (beyond ear tip) | Medium <8 cm |
| Taper of ear: | Average | Average | Average |
| Position of shank (dry husks): | — | Pendent | — |
| Husk color (fresh) 25 days after 50% silking: | Medium green (5GY/5/6) | Light green | Light green (5GY/6/6) |
| Husk color (dry) 65 days after 50% silking: | Buff (2.5Y/8/4) | Buff | Buff |
| Shank length (cm): | 11.4 | 9 | 12.3 |
| Shank (no. of internodes): | — | 7 | — |

F. Kernel (Dried):

|  |  |  |  |
| --- | --- | --- | --- |
| Size (from ear mid-point): |  |  |  |
| Length (cm): | 1.0 | 1.0 | 1.1 |
| Width (cm): | 0.7 | 0.7 | 0.88 |
| Thickness (cm): | 0.4 | 0.4 | 0.36 |
| Shape grade (% rounds): | 39.66 | 20–40 | 45.5 |
| Aleurone color: | Homozygous white | Homozygous white | Homozygous white |
| Endosperm color: | Yellow | Yellow | Yellow |
| Endosperm type: | Normal starch | Normal starch | Normal starch |
| Gm weight/100 seeds (unsized): | 18.2 | 18 | 27.9 |

G. Cob:

|  |  |  |  |
| --- | --- | --- | --- |
| Diameter at mid-point (cm): | 2.7 | 2.2 | — |
| Color: | Light red (10R/5/4) | White | White |

TABLE 1-continued

VARIETY DESCRIPTION INFORMATION FOR INBRED LINE NP 993, NP 899 and A619

| Type: Region Best Adapted: | NP 993 Dent Northcentral | NP 899 Dent Northern and Central | A619 Dent |
|---|---|---|---|
| H. Disease and Insect Resistance: | | | |
| Northern leaf blight: *Exserohilum turcicum* | 9 | 5 | |
| Southern leaf blight: *Bipolaris maydis* | 6 | 7 | |
| Grey leaf spot: *Cercospora zea-maydis* | 6 | 7 | |

The above disease resistance description is based on a scale of 1–9; wherein 1–3 is considered susceptible, 4–5 intermediate, 6–7 resistant and 8–9 highly resistant.

NP 993 most closely resembles Northrup King Co. NP 899 in terms of usage and maturity and may be distinguished from NP 899 by the characteristics summarized in Table 1 above. NP 899 is a Northrup King Co. proprietary line and is further disclosed in U.S. Pat. No. 5,530,181, issued Jun. 25, 1996 and having ATCC accession number 97362.

With respect to publically available inbred lines, NP 993 most closely resembles A619. However, these lines differ in a number of characteristics. Some of the characteristics between NP 993 and A619 are summarized in Table 1.

This invention is also directed to methods for producing a corn plant by crossing a first parent corn plant with a second parent corn plant, wherein the first or second corn plant is a corn plant of the inbred line NP 993. However, both first and second parent corn plant can come from the inbred corn line NP 993. Therefore any methods using NP 993 are part of this invention including self-pollination, backcross-pollination, hybrid breeding and crosses to populations. It may be desirable to use a male-sterile (either cytoplasmic or nuclear) female parent to prevent self-pollination. If the female is not male-sterile, then either physical or chemical steps may be taken to ensure that self-pollination does not occur. Any plants produced using inbred corn line NP 993 as a parent are within the scope of this invention including any plant produced by the use of cells, protoplasts or tissue from NP 993.

Specifically NP 993 produces hybrids that are competitive yielding. In general, hybrids have good stalk quality and may have characteristic reddish stalks late in the growing season as opposed to greenish stalks. Slightly short husks which expose a small part of the ear tip has also been observed on hybrids produced from NP 993. Additionally some resistance has been observed with respect to Stewarts Bacterial Wilt.

The techniques used to obtain the corn hybrid seeds and plants of this invention are conventional in the seed industry and are well known to those skilled in the art. The two parent lines are planted in pollinating proximity to each other in alternating sets of rows; however, any convenient planting pattern that allows for the free transfer of pollen is acceptable. The plants of both inbred lines are allowed to grow until the time of flowering. At flowering, tassels are removed from all plants of the female parent by hand, machine or other means. Natural cross-pollination is allowed to occur. Ears from the female plants are harvested to obtain novel $F_1$ hybrid corn seeds of the present invention. $F_1$ hybrid corn plants of the invention are obtained by planting seeds harvested from the female plant.

An example of a competitive yielding hybrid of this invention is that produced by the cross Northrup King Co. Inbred line H8431 X NP 993, hereinafter H8431 X NP 993. Inbred H8431 has PVP Certificate No. 8800032 which is hereby incorporated by reference. The hybrid produced from H8431 X NP 993 is a 105 Minnesota Relative Maturity (RM) single cross hybrid. This hybrid most closely resembles the commercially available Northrup King Co. hybrid N4242. N4242 is sold in the Northern U.S. and Canada. The hybrid produced by the cross (H8431 X NP 993) has significantly higher yield performance, and slightly higher moisture compared to N4242. In Table 2 below, some of the results are indicated for (H8431 X NP 993) compared to N4242 and other similar hybrids. H8431 X NP 993 is significantly different from N4242 for yield and moisture. N5220 is a commercially available Northrup King Co. hybrid made by the cross NP 901 X NP 899 and having ATCC Acessesion Nos. 97364, 97363, and 97362 respectively and further disclosed in U.S. Pat. No. 5,530,181 issued Jun. 25, 1996.

TABLE 2

Combined Location and Year Performance Data
(1994 1995; 50 environments; 100–110 RM Markets)

| Hybrid | YLD | MST (bu/a) | STK (BR) % | RT | Pit Ht (cm) | Silk HU | STBW |
|---|---|---|---|---|---|---|---|
| H8431 X NP 993 | 170 | 18.9 | 3 | 1 | 264 | 1319 | 6.0 |
| N4242 | 162 | 18.2 | 3 | 1 | 270 | 1282 | 8.0 |
| N5220 | 170 | 21.3 | 3 | 4 | 293 | 1341 | 4.5 |
| P3769 | 157 | 18.4 | 4 | 4 | 263 | 1249 | — |
| P3573 | 169 | 20.4 | 4 | 2 | 284 | 1334 | 5.5 |
| Trails with data: | 50 | 50 | 45 | 39 | 11 | 11 | 1 |
| LSD | 5 | 0.4 | 1 | 2 | 8 | 16 | |

STBW = Stewarts Bacterial Wilt, a rating of 1 = best resistance, 9 = most suspectible.

As used herein the term plant includes plant cells, plant protoplasts, plant cell tissue cultures including that from which corn plants fertile or otherwise can be regenerated, plant calli and plant cell clumps, and differentiated forms of plants such as, but not limited to embryos, pollen, stamen, anthers, flowers, kernels, ears, cobs, leaves, stalks, roots, shoots, plantlets, silks and kernels.

Methods of cell and tissue culture and regeneration are well known in the art and described for example in "Plant Tissue Culture Manual: Fundamentals and Application", Ed. K. Lindsey, Kluwer (1991) and in Green and Rhodes, "Plant Regeneration in Tissue Culture of Maize", Maize for Biological Research (Plant Molecular Biology Association, Charlottesville, Va., 1982, pp. 367–372), which are hereby incorporated by reference.

As is well known corn can be put to a wide variety of uses not only as livestock feed but also for human consumption of corn kernels and as a raw material in industry. Both grain and non-grain portions of the plant are used as a livestock feed for swine, cattle and poultry. In the food industry corn is used in wet and dry milling. In wet milling there is the separation of the germ, hull gluten and starch. Germ is used to produce corn oil and germ cake for feed. Corn starch may be packaged for human consumption or used in food products such as sauces, gravies, puddings, sweeteners, syrups, and baking powder. Other nonedible uses include textiles, paper, adhesives, cosmetics, explosives, corn binders, laundry purposes and agricultural formulations. Dry milling is used to produce breakfast foods, grits, cornmeal and corn flour. Other uses of corn include fuel, in the form of fuel alcohol or ethanol; seed; alcoholic beverages and construction.

DEPOSIT INFORMATION

Deposits of at least 2500 seeds of inbred NP 993, has been made unrestrictedly available to the public via the American Type Culture Collection (ATCC), Rockville, Md. 20852 USA. The deposit corresponds to ATCC Deposit No. 209542, ATCC and was made on Dec. 10, 1997. The seeds are from stock maintained by Northrup King since prior to filing this application or any parents thereof. The deposit of inbred corn line NP 993 will be maintained in the ATCC depository, which is a public depositary, for a period of 30 years, or 5 years after the most recent request, or for enforceable life of the patent, whichever, is longer, and will be replaced if it ever becomes nonviable during that period. Additionally, with respect to Plant Variety Protection Certificates received and applied for, Applicant does not waive any infringement of its rights granted under this patent or under the Plant Variety Protection Act (7 U.S.C. 2312 et seq.).

It is claimed:

1. Seed of corn line designated NP 993 and having ATCC Accession No. 209542.

2. Parts of a corn plant produced by the seed of corn line designated NP 993 and having ATCC Accession No. 209542 according to claim 1.

3. A corn plant produced by the seed of the plant of claim 2.

4. An inbred corn plant having all the physiological and morphological characteristics of a corn plant produced by seed of corn line designated NP 993 having ATCC Accession No. 209542.

5. Hybrid seed produced by crossing plants of inbred corn line designated NP 993, the seed having ATCC Accession No. 209542 and plants of another inbred corn line having a genotype different from corn line NP 993.

6. Pollen of the corn plant of claim 3.

7. A tissue culture of regenerable cells of the corn plant according to claim 3, wherein the regenerated corn cells have a genotype capable of expressing all the physiological and morphological characteristics of the corn plant of claim 3, the seed of which has been deposited and having ATCC Accession No. 209542.

8. A corn plant regenerated from the tissue culture of claim 7.

9. Hybrid seeds of claim 5 wherein the corn line NP 993 having ATCC Accession No. 209542 is the male parent.

10. Hybrid corn plants grown from the seed of claim 5.

11. A tissue culture of regenerable cells of the corn plant of claim 10.

12. Seeds produced by the cultivation of the hybrid plant of claim 10.

13. A first generation hybrid corn plant produced by growing hybrid corn seed, wherein said seed is produced by crossing a first inbred parent corn plant with a second inbred parent corn plant wherein said first or second inbred corn plant is the corn plant of claim 3, and harvesting the resultant hybrid seed.

14. A method of producing novel hybrid corn seed comprising:
   a. planting in pollinating proximity seeds of inbred corn line NP 993 having ATCC Accession No. 20954 and a second inbred line having a genotype different from NP 993;
   b. cultivating corn plants resulting from said planting until time of flowering;
   c. emasculating said flowers of plants of said second inbred line;
   d. allowing cross pollination to occur between said inbreds, and
   e. harvesting the seeds produced on said plants of the second inbred line.

15. The hybrid corn seeds produced by the method of claim 14.

16. A tissue culture of claim 7 wherein the tissue culture is selected from the group consisting of leaves, pollen, embryos, anthers, silks, flowers, roots, root tips, stalks, kernels, cells and protoplasts thereof.

* * * * *